(12) United States Patent
Bucci et al.

(10) Patent No.: US 9,421,043 B2
(45) Date of Patent: Aug. 23, 2016

(54) FLEXIBLE AND STATIC INTERSPINOUS/INTER-LAMINAR SPINAL SPACERS

(71) Applicant: Life Spine, Inc., Hoffman Estates, IL (US)

(72) Inventors: Kara A. Bucci, Chicago, IL (US); Madeline Wolters, Carol Stream, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 49 days.

(21) Appl. No.: 14/281,619

(22) Filed: May 19, 2014

(65) Prior Publication Data

US 2015/0018883 A1    Jan. 15, 2015

Related U.S. Application Data

(63) Continuation of application No. 13/567,581, filed on Aug. 6, 2012, now Pat. No. 8,728,123, which is a continuation of application No. 12/694,051, filed on Jan. 26, 2010, now Pat. No. 8,236,031.

(60) Provisional application No. 61/147,384, filed on Jan. 26, 2009.

(51) Int. Cl.
*A61B 17/70*        (2006.01)
*A61B 17/56*        (2006.01)

(52) U.S. Cl.
CPC ......... *A61B 17/7062* (2013.01); *A61B 17/7068* (2013.01); *A61B 2017/564* (2013.01)

(58) Field of Classification Search
CPC ........... A61B 17/7062; A61B 17/7067; A61B 17/7068

USPC ............. 606/246–249, 279; 623/17.11–17.16
See application file for complete search history.

(56) References Cited

U.S. PATENT DOCUMENTS

| 4,466,426 A | 8/1984 | Blackman |
| 4,636,217 A | 1/1987 | Ogilvie et al. |

(Continued)

FOREIGN PATENT DOCUMENTS

WO    WO-2006/102485        9/2006

OTHER PUBLICATIONS

"Bacfuse® Spinous Process Fusion Plate Surgical Technique", © 2011, Pioneer Surgical, 12 pages.

*Primary Examiner* — Ellen C Hammond
*Assistant Examiner* — Christina Negrellirodrigue
(74) *Attorney, Agent, or Firm* — Foley & Lardner LLP

(57) ABSTRACT

Interspinous/inter-laminar spinal spacers are configured to be placed between bony structures of adjacent vertebrae. In one form, spinal spacers are defined by a unitary body comprising a first contoured plate and a second contoured plate. The first contoured plate comprises first and second wings configured to engage first and second vertebra, and a post extending from the contoured plate and having a bullet nose and an outer surface with a curved portion and a planar portion. The second contoured plate is slidably coupled to the post of the body and comprises first and second wings configured to engage first and second vertebra, a rear portion extending between the first wing and the second wing, and a front portion extending between the first wing and the second wing. The first wing, second wing, rear portion, and front portion define a first bore configured to receive the post.

17 Claims, 7 Drawing Sheets

(56) References Cited

U.S. PATENT DOCUMENTS

| | | |
|---|---|---|
| 5,645,599 A | 7/1997 | Samani |
| 5,836,948 A | 11/1998 | Zucherman et al. |
| 5,860,977 A | 1/1999 | Zucherman et al. |
| 5,876,404 A | 3/1999 | Zucherman et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,451,019 B1 | 9/2002 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,743,257 B2 | 6/2004 | Castro |
| 6,796,983 B1 | 9/2004 | Zucherman et al. |
| 7,101,375 B2 | 9/2006 | Zucherman et al. |
| 7,695,513 B2 | 4/2010 | Zucherman et al. |
| 8,231,656 B2 * | 7/2012 | Lee .................. A61B 17/7068 606/249 |
| 8,603,142 B2 * | 12/2013 | Robinson ........... A61B 17/7068 606/249 |
| 2003/0236520 A1 | 12/2003 | Lim et al. |
| 2005/0222681 A1 | 10/2005 | Richley et al. |
| 2005/0261768 A1 | 11/2005 | Trieu |
| 2005/0261769 A1 | 11/2005 | Moskowitz et al. |
| 2005/0278036 A1 | 12/2005 | Leonard et al. |
| 2006/0036258 A1 | 2/2006 | Zucherman et al. |
| 2006/0084988 A1 | 4/2006 | Kim |
| 2006/0089718 A1 | 4/2006 | Zucherman et al. |
| 2006/0241601 A1 | 10/2006 | Trautwein et al. |
| 2006/0264938 A1 | 11/2006 | Zucherman et al. |
| 2006/0293662 A1 | 12/2006 | Boyer et al. |
| 2007/0142915 A1 | 6/2007 | Altarac et al. |
| 2007/0173823 A1 | 7/2007 | Dewey et al. |
| 2008/0114456 A1 | 5/2008 | Dewey et al. |
| 2008/0161818 A1 | 7/2008 | Kloss et al. |
| 2008/0177391 A1 | 7/2008 | Mitchell et al. |
| 2008/0183211 A1 * | 7/2008 | Lamborne .......... A61B 17/7068 606/249 |
| 2008/0312741 A1 | 12/2008 | Lee et al. |
| 2009/0270919 A1 | 10/2009 | Dos Reis, Jr. |
| 2010/0004688 A1 | 1/2010 | Maas et al. |
| 2010/0036419 A1 | 2/2010 | Patel et al. |
| 2010/0204732 A1 | 8/2010 | Aschmann et al. |
| 2010/0241167 A1 | 9/2010 | Taber et al. |
| 2011/0022090 A1 | 1/2011 | Gordon et al. |
| 2011/0066186 A1 | 3/2011 | Boyer et al. |
| 2011/0144692 A1 | 6/2011 | Saladin et al. |
| 2011/0172709 A1 | 7/2011 | Lyons et al. |
| 2011/0184468 A1 | 7/2011 | Metcalf et al. |

* cited by examiner

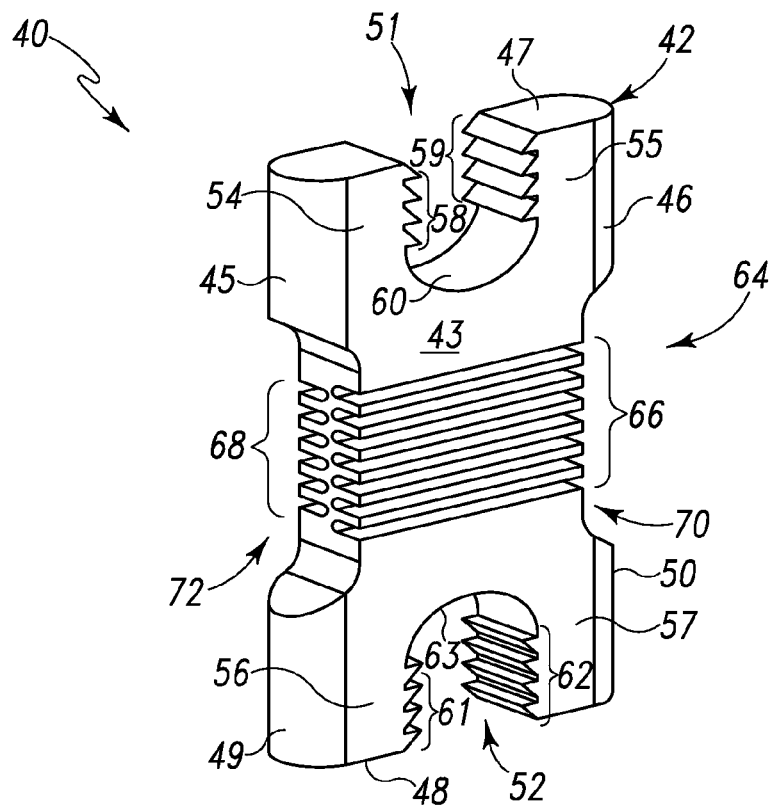
Fig. 4
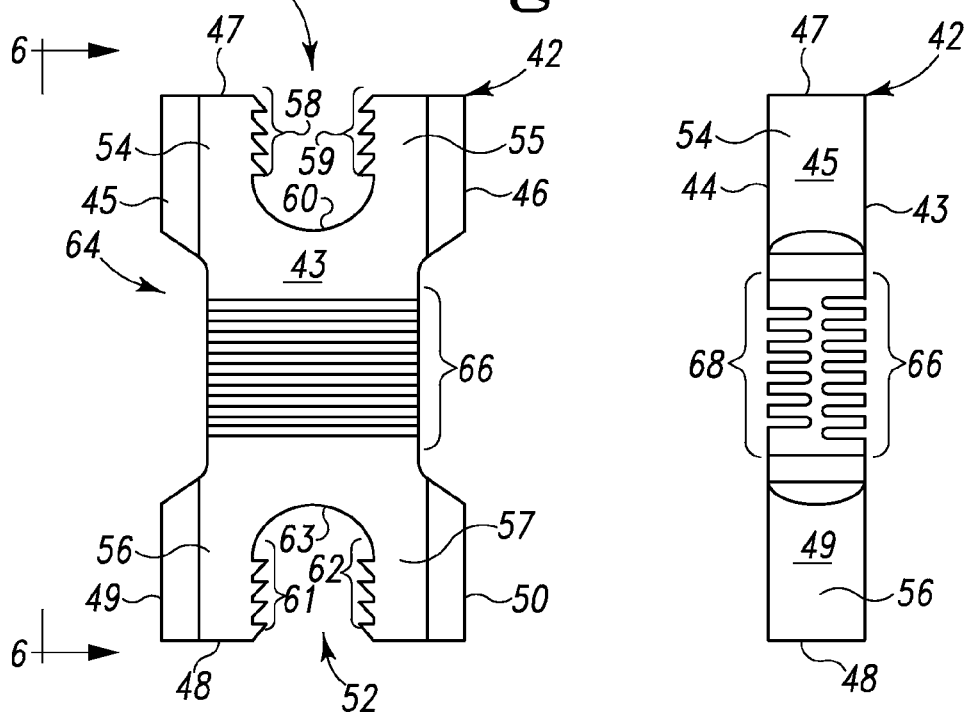 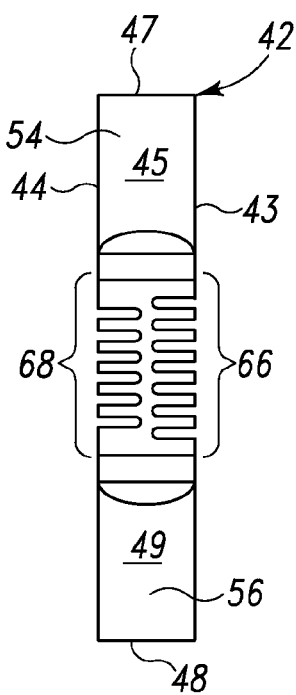
Fig. 5  Fig. 6

FLEXIBLE AND STATIC INTERSPINOUS/INTER-LAMINAR SPINAL SPACERS

CROSS-REFERENCE TO RELATED APPLICATIONS

This patent application is a continuation of U.S. patent application Ser. No. 13/567,581, filed Aug. 6, 2012, which is a continuation of U.S. patent application Ser. No. 12/694,051 filed on Jan. 26, 2010, and titled Flexible And Static Interpinous/Inter-Laminar Spinal Spacers, which claims the benefit of and/or priority to U.S. Provisional Patent Application No. 61/147,384 filed Jan. 26, 2009 and titled "Flexible Interspinous/Inter-Laminar Spinal Spacer," the entire contents of all of these applications are specifically hereby incorporated herein by reference.

BACKGROUND

The present invention relates to devices for the spine and, more particularly, to spinal implants for providing interspinous and/or inter-laminar space between adjacent vertebrae.

As we age various changes can occur in the body. For instance, the ligaments of the spine can thicken and calcify (i.e. harden from deposits of calcium), bone and joints may enlarge, bone spurs called osteophytes may form, spinal discs may collapse and bulge (i.e. herniate) or one vertebra may slip over another (spondylolisthesis). Any one or these conditions and/or others can cause what is known as lumbar spinal stenosis. Lumbar spinal stenosis is a narrowing of the bony spinal canal. While some people are born with this condition, most often spinal stenosis is the result of one of the above-identified degenerative conditions that develop in mainly the middle-aged and elderly population.

In this regard, spinal stenosis may be considered as the gradual result of aging and "wear and tear" on the spine from everyday activities. Such degenerative or age-related changes in our bodies can lead to compression of nerves (i.e. pressure on the nerves that can cause pain and/or damage). Symptoms of lumbar spinal stenosis include leg pain ("pins and needles") that can limit standing, walking, self-supporting daily activities, work social and recreational pursuits. Lack of activity because of lumbar spinal stenosis may lead to obesity, depression and general physical deterioration. Surgical procedures may be used in order to alleviate the problems associated with spinal stenosis. This may include the use of an implant designed to hold or stabilize adjacent vertebrae or vertebral parts of the spine.

Other spinal conditions, diseases and/or accidents, however, can also cause problems that may require spinal surgery and the need to hold or stabilize adjacent vertebrae or vertebral parts in a spatial orientation relative to one another and/or with regard to other vertebral parts. In these cases, the surgeon may again use a device to hold or stabilize adjacent vertebrae or vertebral parts. The implants used for these purposes are typically not affixed to the vertebrae by bone screws or the like but are held to the vertebrae by the bony portions, structures or protrusions of the vertebrae.

Of these types of spinal devices some allow for movement between the adjacent vertebrae to which it is connected and some do not. The static spinal device provides a fixed or static spatial orientation of the adjacent vertebrae to which it is affixed. The static spinal devices permanently limit movement between the adjacent vertebrae to which it is affixed. The non-static spinal devices provide limited movement between the adjacent vertebrae in addition to maintaining a spatial orientation of the adjacent vertebrae. These non-static spinal devices, however, are assemblies formed of two or more components with a variety of ways to achieve motion between the various components.

In view of the above, it is apparent that there is a need for improved interspinous or inter-laminar spinal devices, both flexible and static one-piece designs.

SUMMARY

The present invention provides interspinous/inter-laminar spinal spacers (processes, transverse and spinous—i.e. spinal spacers) that are configured to be placed between bony structures of adjacent vertebrae of a spine.

In one form, a flexible interspinous/inter-laminar spinal spacer (processes, transverse and spinous—i.e. flexible spinal spacer) is defined by a unitary body that is configured to be placed between bony structures of adjacent vertebrae of a spine. The unitary body has a flex portion that provides for motion between the adjacent vertebrae to which it is coupled. The flex portion is configurable to provide for various degrees of angulation, flexion, extension and/or compression of the present flexible spinal spacer. Thus, the present flexible spinal spacer allows for controlled movement of the adjacent vertebrae to which it is attached, as well as aid in insertion and/or implantation of the flexible spinal spacer.

The flex portion may take different configurations depending on the type, degree and/or amount of flexure. In one form, the flex portion comprises a plurality of cuts, slits, grooves, channels, notches or the like (collectively, cuts) extending from lateral sides of the unitary body that may or may not be through. The cuts are staggered relative to opposite serrations and may or may not extend diagonally from and along the lateral sides. The size of the cuts, the degree of slant or no slant of the cuts all provides various flexure properties. This allows for various degrees of lateral compression of the flexible spinal spacer. Other configurations are thus contemplated that provide for lateral compression and/or extension of the flexible spinal spacer.

In another form, the flex portion comprises a plurality of posterior and anterior ribs, ledges, shelves, fins, projections or the like (collectively, ribs) extending from a middle section of the unitary body. The ribs are staggered relative to opposite ribs and extend generally perpendicular to the middle section (i.e. in the posterior and anterior direction). The number and size of the anterior/posterior ribs all provide various flexure properties. This allows for various degrees of extension and/or flexion of the flexible spinal spacer. Other configurations are thus contemplated that provide for flexion and/or extension of the flexible spinal spacer.

In another form, the flex portion comprises posterior and anterior flexure contours (e.g. springs or spring-like contours) defined by the posterior and anterior sides of the unitary body. The posterior and anterior flexure contours extend generally from and between the superior end and the inferior end of the unitary body. Each flexure contour comprises one or more curvatures. The number, size, thickness and configuration of the curvatures all provide various flexure properties. A cavity is thus formed between the posterior flexure contour and the anterior flexure contours of the unitary body. This allows for various degrees of angulation, compression, flexion and/or extension of the flexible spinal spacer. Other configurations are thus contemplated that provide for angulation only or angulation, compression, flexion and/or extension of the flexible spinal spacer.

The unitary body of the flexible spinal spacers has saddle-shaped ends each defining a pocket that is configured to receive a bony structure of a vertebra. The pockets may or may not be textured and/or may or may not include teeth, serrations or ridged surfaces to secure the spinal spacer to the bony structure.

The present flexible spinal spacers allow for controlled movement of the adjacent vertebrae to which it is attached, as well as aid in insertion and/or implantation of the flexible spinal spacer.

In another form, static interspinous/inter-laminar spinal spacers (processes, transverse and spinous—i.e. static spinal spacers) are defined by a unitary body that is configured to be placed between bony structures of adjacent vertebrae of a spine. The unitary body has saddle-shaped ends each defining a pocket that is configured to receive a bony structure of a vertebra. The pockets may or may not be textured and/or may or may not include teeth, serrations or ridged surfaces to secure the spinal spacer to the bony structure.

The present spinal spacers are made from a biocompatible material such as PEEK (PolyEtherEtherKetone), titanium, stainless steel or the like that will provide flexure given the geometry or configuration of the unitary body thereof.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein:

FIG. 4 is an isometric view of another embodiment of a flexible interspinous/inter-laminar spinal spacer (processes, transverse & spinous—i.e. flexible spinal spacer) fashioned in accordance with the principles of the present invention;

FIG. 5 is a front view of the flexible spinal spacer of FIG. 4;

FIG. 6 is a side view of the flexible spinal spacer of FIG. 4 taken along line 6-6 of FIG. 5;

Like reference numerals indicate the same or similar parts throughout the several figures.

A discussion of the features, functions and/or configurations of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF THE EXEMPLARY EMBODIMENTS

Figure 1:
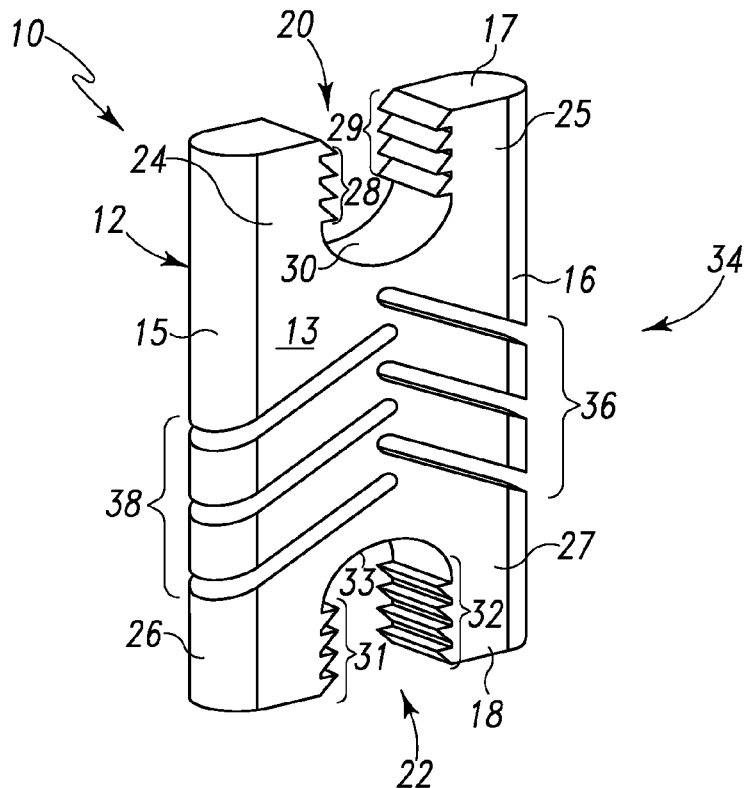
FIG. 1 is an isometric view of an embodiment of a flexible interspinous/inter-laminar spinal spacer (processes, transverse & spinous—i.e. flexible spinal spacer) fashioned in accordance with the principles of the present invention.
Figure 2:
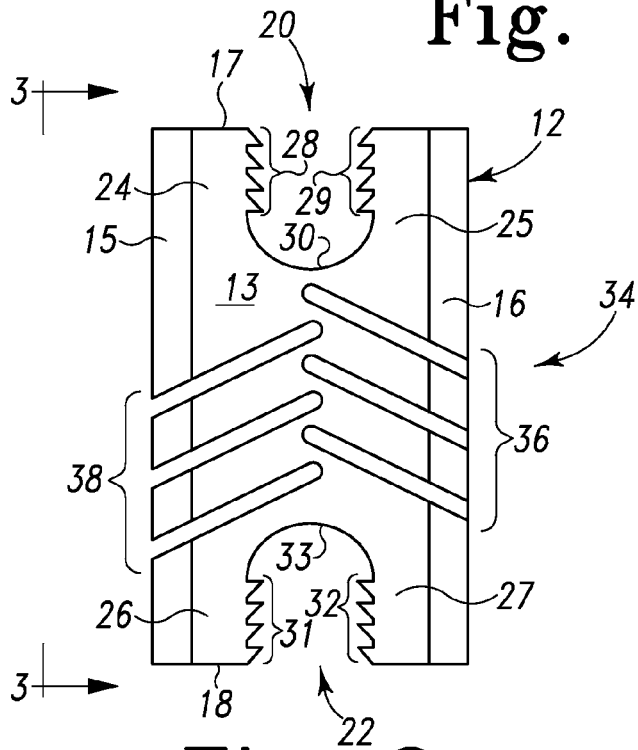
FIG. 2 is a front view of the flexible spinal spacer of FIG. 1.
Figure 3:
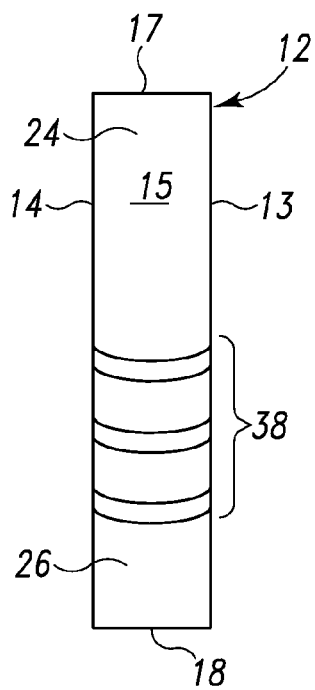
FIG. 3 is a side view of the flexible spinal spacer of FIG. 1 taken along line 3-3 of FIG. 2.

Referring to FIGS. 1-3, there is shown an embodiment of a flexible interspinous or inter-laminar spinal spacer (processes, transverse and spinous—i.e. flexible spinal spacer) generally designated 10 fashioned in accordance with the principles of the present invention. The flexible spinal spacer 10 is used as an interspinous, inter-laminar, interbody, or interbony spinal spacer and thus is configured to be placed between bony structures of adjacent vertebrae of a spine.

The flexible spinal spacer 10 is formed as a unitary or single-piece body 12 of a biocompatible material. The body 12 is formed in a generally "H" shape and thus defines a first lateral side 15, a second lateral side 16, a posterior side 13, an anterior side 14, a superior side or end 17, and an inferior side or end 18. It should be appreciated that the flexible spinal spacer may take forms other than an "H" while maintaining the features and/or characteristics of the present invention. The body 12 also has a flex portion 34 disposed between the superior side 17 and the inferior side 18. The flex portion 34 has flexure characteristics/properties that provide for relative movement or motion of the spinal spacer 10 and thus motion or movement between the adjacent vertebrae to which it is connected. The flex portion 34 is configurable to provide for various degrees of angulation and/or compression of the body 12.

The flex portion 34 comprises a first set, number, or plurality of cuts, slits, grooves, channels, notches or the like 36 (collectively, cuts 36) and a second set, number, or plurality of cuts, slits, grooves, channels, notches or the like 38 (collectively, cuts 38) in the posterior and anterior sides 13, 14 of the body 12. In FIGS. 1-3, the first and second plurality of cuts 36, 38 extend diagonally into the body 12 from the lateral sides 15 and 16 thereof. It should be appreciated that the cuts 36, 38 may be horizontal cuts, perpendicular cuts and/or a pattern of cuts to achieve angulation, flexion, extension and/or compression of the body 12. Also, while three (3) cuts are shown for both the first and second set of cuts 36, 38, it should be appreciated that the number of cuts may vary depending on the desired amount and/or type of flexure.

The superior end 17 is formed as a saddle-shape defining first and second legs 24, 25 separated by a pocket 20 that is configured to receive a bony structure of a superior situated vertebra. The first and second legs 24 and 25 define first and second lateral sides of the pocket 20 with a curved bottom 30. The first lateral side of the pocket 20 has a first plurality of teeth, serrations or ridged surfaces 28 (collectively, teeth) along its length. The first plurality of teeth 28 provide for connection to a first portion of a bony vertebral structure. The second lateral side of the pocket 20 has a second plurality of teeth, serrations or ridged surfaces 29 (collectively, teeth) along its length. The second plurality of teeth 29 provide for connection to a second portion of the bony structure of the superior situated vertebra. The sides of the pocket 20 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony structure of the superior situated vertebra.

The inferior end 18 is formed as a saddle-shape defining third and fourth legs 26, 27 separated by a pocket 22 that is configured to receive a bony structure of an inferior situated vertebra (adjacent to the superior situated vertebra). The third and fourth legs 26 and 27 define first and second lateral sides of the pocket 22 with a curved bottom 33. The first lateral side of the pocket 22 has a first plurality of teeth, serrations or ridged surfaces 31 (collectively, teeth) along its length. The first plurality of teeth 31 provide for connection to a first portion of a bony structure of the inferior vertebra. The second lateral side of the pocket 22 has a second plurality of teeth, serrations or ridged surfaces 32 (collectively, teeth) along its length. The second plurality of teeth 32 provide for connection to a second portion of the bony structure of the inferior situated vertebra. The sides of the pocket 22 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony vertebral structure.

The flexible spinal spacer 10 is thus configured to provide for various degrees of angulation, flexion, extension and/or compression. Thus, the present flexible spinal spacer allows for controlled movement of the adjacent vertebrae to which it is attached (the superior and inferior situated vertebra), as well as aid in insertion and/or implantation of the flexible spinal spacer.

Referring to FIGS. 4-6, there is shown another embodiment of a flexible interspinous or inter-laminar spinal spacer (processes, transverse and spinous—i.e. flexible spinal spacer) generally designated 40 fashioned in accordance with the principles of the present invention. The flexible spinal spacer 40 is used as an interspinous, inter-laminar, interbody, or interbony spinal spacer and thus is configured to be placed between bony structures of adjacent vertebrae of a spine.

The flexible spinal spacer 40 is formed as a unitary or single-piece body 42 of a biocompatible material. The body 42 is formed in a generally "H" shape and thus defines a first superior lateral side 45, a second superior lateral side 46, a first inferior lateral side 49, a second inferior lateral side 50, a posterior side 43, an anterior side 44, a superior side or end 47, and an inferior side or end 48. It should be appreciated that the flexible spinal spacer may take forms other than an "H" while maintaining the features and/or characteristics of the present invention. The body 42 also has a flex portion 64 disposed between the superior side 47 and the inferior side 48. The flex portion 64 has flexure characteristics/properties that provide for relative movement or motion of the spinal spacer 40 and thus motion or movement between the adjacent vertebrae to which it is connected. The flex portion 64 is configurable to provide for various degrees of angulation and/or compression of the body 42.

The flex portion 64 includes a first set, number, or plurality of ribs, ledges, shelves, fins, projections or the like 66 (collectively, ribs 66) [conversely, and/or additionally, a plurality of grooves, slits, channels or the like 66 (collectively, grooves 66) on the posterior side 43 of the body 42 and extending outwardly from a middle portion or section thereof (i.e. extending in the posterior direction). The flex portion 64 further includes a second set, number, or plurality of ribs, ledges, shelves, fins, projections or the like 68 (collectively, ribs 68) [conversely, and/or additionally, a plurality of grooves, slits, channels or the like 68 (collectively, grooves 68) on the anterior side 44 of the body 42 and extending outwardly from the middle portion or section thereof (i.e. extending in the anterior direction). This provides for various flexure properties.

In FIGS. 4-6, the first and second plurality of ribs/grooves 66, 68 extend perpendicular relative to the posterior/anterior faces of the body 42. It should be appreciated that the location and/or shape of the ribs/grooves 66, 68 may be fashioned differently if desired to achieve angulation, flexion, extension and/or compression of the body 42. Also, the number of ribs/grooves and their configuration may vary depending on the desired amount and/or type of flexure and/or flexure properties. Additionally, a first cutout, cavity or depression 72 is defined between the lateral sides 46 and 50 at the junction of the ribs/grooves 66 and ribs/grooves 68 (flex portion 64), while a second cutout, cavity or depression 70 is defined between the lateral sides 45 and 49 at the junction of the ribs/grooves 66 and ribs/grooves 68 (flex portion 64). It should be appreciated that the shape of the cutouts 70, 72 may be fashioned differently than shown to achieve a desired amount and/or type of flexure and/or flexure properties (angulation, flexion, extension and/or compression) of the body 42.

The superior end 47 is formed as a saddle-shape defining first and second legs 54, 55, with leg 54 having the first superior lateral side 45 and leg 55 having the second superior lateral side 46, the legs 54, 55 separated by a pocket 51 that is configured to receive a bony structure of a superior situated vertebra. The first and second legs 54 and 55 define first and second lateral sides of the pocket 51 with a curved bottom 60. The first lateral side of the pocket 51 has a first plurality of teeth, serrations or ridged surfaces 58 (collectively, teeth) along its length. The first plurality of teeth 58 provide for connection to a first portion of a bony vertebral structure. The second lateral side of the pocket 51 has a second plurality of teeth, serrations or ridged surfaces 59 (collectively, teeth) along its length. The second plurality of teeth 59 provide for connection to a second portion of the bony structure of the superior situated vertebra. The sides of the pocket 51 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony structure of the superior situated vertebra.

The inferior end 48 is formed as a saddle-shape defining third and fourth legs 56, 57, with leg 56 having the first inferior lateral side 49 and leg 57 having the second inferior lateral side 50, the legs 56, 57 separated by a pocket 52 that is configured to receive a bony structure of an inferior situated vertebra (adjacent to the superior situated vertebra). The third and fourth legs 56 and 57 define first and second lateral sides of the pocket 52 with a curved bottom 63. The first lateral side of the pocket 52 has a first plurality of teeth, serrations or ridged surfaces 61 (collectively, teeth) along its length. The first plurality of teeth 61 provide for connection to a first portion of a bony structure of the inferior vertebra. The second lateral side of the pocket 52 has a second plurality of teeth, serrations or ridged surfaces 62 (collectively, teeth) along its length. The second plurality of teeth 62 provide for connection to a second portion of the bony structure of the inferior situated vertebra. The sides of the pocket 52 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony vertebral structure.

The flexible spinal spacer 40 is thus configured to provide for various degrees of angulation, flexion, extension and/or compression. Thus, the present flexible spinal spacer allows for controlled movement of the adjacent vertebrae to which it is attached (the superior and inferior situated vertebra), as well as aid in insertion and/or implantation of the flexible spinal spacer.

Figure 7:
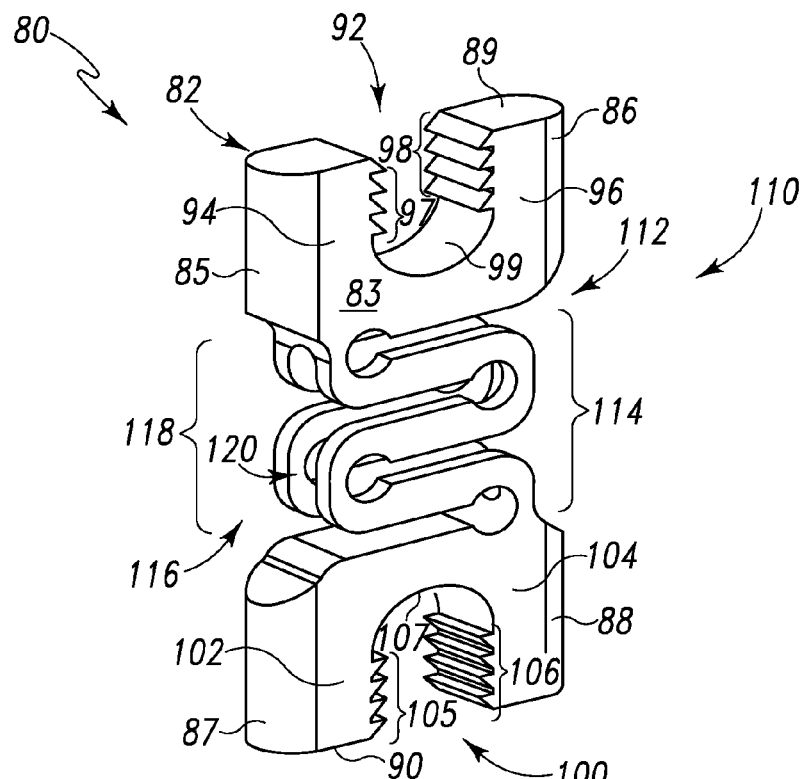
FIG. 7 is an isometric view of another embodiment of a flexible interspinous/inter-laminar spinal spacer (processes, transverse & spinous—i.e. flexible spinal spacer) fashioned in accordance with the principles of the present invention.
Figure 8:
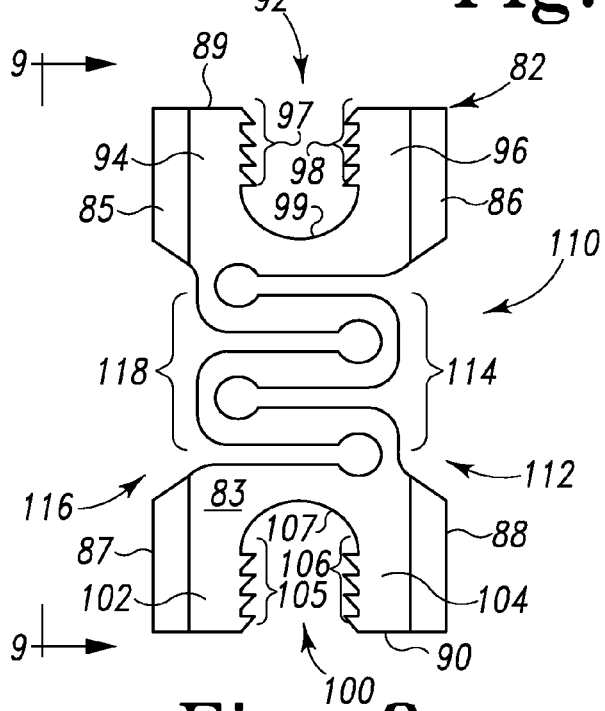
FIG. 8 is a front view of the flexible spinal spacer of FIG. 7.
Figure 9:
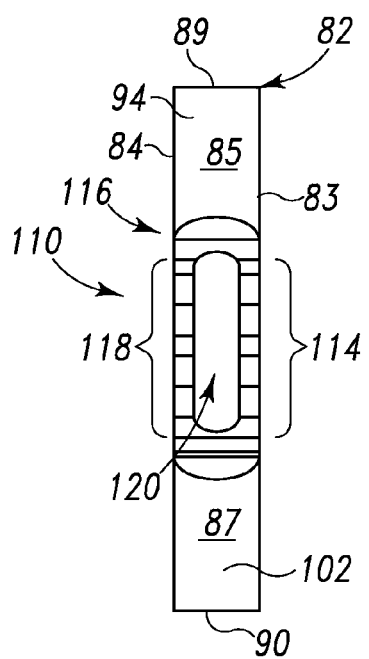
FIG. 9 is a side view of the flexible spinal spacer of FIG. 7 taken along line 9-9 of FIG. 8.

Referring to FIGS. 7-9, there is shown another embodiment of a flexible interspinous or inter-laminar spinal spacer (processes, transverse and spinous—i.e. flexible spinal spacer) generally designated 80 fashioned in accordance with the principles of the present invention. The flexible spinal spacer 80 is used as an interspinous, inter-laminar, interbody, or interbony spinal spacer and thus is configured to be placed between bony structures of adjacent vertebrae of a spine.

The flexible spinal spacer 80 is formed as a unitary or single-piece body 82 of a biocompatible material. The body 82 is formed in a generally "H" shape and thus and thus defines a first superior lateral side 85, a second superior lateral side 86, a first inferior lateral side 87, a second inferior lateral side 88, a posterior side 83, an anterior side 84, a superior side or end 89, and an inferior side or end 90. It should be appreciated that the flexible spinal spacer may take forms other than an "H" while maintaining the features and/or characteristics of the present invention. The body 82 also has a flex portion 110 disposed between the superior side 89 and the inferior side 90. The flex portion 110 has flexure characteristics/properties that provide for relative movement or motion of the spinal spacer 80 and thus motion or movement between the adjacent vertebrae to which it is connected. The flex portion 110 is configurable to provide for various degrees of angulation and/or compression of the body 82.

The flex portion 110 comprises a first flexure contour 114 (e.g. spring or spring-like contours 114) defined by and in the posterior side 83 of the unitary body 82 and a second flexure contour 118 (e.g. springs or spring-like contours 118) defined by the anterior side 84 of the unitary body 82. In FIGS. 7-9, the first and second flexure contours 114, 118 extend from the superior end 89 to the inferior end 90. It should be appreciated that the shape and/or configuration of the flexure contours 114, 118 may be fashioned differently if desired to achieve angulation, flexion, extension and/or compression of the body 82. A cavity 120 is defined between the flexure contours 114, 118. The number of contours and their configuration may vary depending on the desired amount and/or type of flexure and/or flexure properties.

Additionally, a first cutout, cavity or depression 112 is defined between the lateral sides 86 and 88 at the junction of the flexure contours 114, 118 (flex portion 110), while a second cutout, cavity or depression 116 is defined between the lateral sides 85 and 87 at the junction of the flexure contours 114, 118 (flex portion 110). It should be appreciated that the shape of the cutouts 114, 116 may be fashioned differently than shown to achieve a desired amount and/or type of flexure and/or flexure properties (angulation, flexion, extension and/or compression) of the body 82.

The superior end 89 is formed as a saddle-shape defining first and second legs 94, 96 with leg 94 having the first inferior lateral side 85 and leg 96 having the second inferior lateral side 86, the legs 94, 96 separated by a pocket 92 that is configured to receive a bony structure of a superior situated vertebra. The first and second legs 94 and 96 define first and second lateral sides of the pocket 92 with a curved bottom 99. The first lateral side of the pocket 92 has a first plurality of teeth, serrations or ridged surfaces 97 (collectively, teeth) along its length. The first plurality of teeth 97 provide for connection to a first portion of a bony vertebral structure. The second lateral side of the pocket 92 has a second plurality of teeth, serrations or ridged surfaces 97 (collectively, teeth) along its length. The second plurality of teeth 97 provide for connection to a second portion of the bony structure of the superior situated vertebra. The sides of the pocket 92 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony structure of the superior situated vertebra.

The inferior end 90 is formed as a saddle-shape defining third and fourth legs 102, 104, with leg 102 having the first inferior lateral side 87 and leg 104 having the second inferior lateral side 88, the legs 102, 104 separated by a pocket 100 that is configured to receive a bony structure of an inferior situated vertebra (adjacent to the superior situated vertebra). The third and fourth legs 102 and 104 define first and second lateral sides of the pocket 100 with a curved bottom 107. The first lateral side of the pocket 100 has a first plurality of teeth, serrations or ridged surfaces 105 (collectively, teeth) along its length. The first plurality of teeth 105 provide for connection to a first portion of a bony structure of the inferior vertebra. The second lateral side of the pocket 100 has a second plurality of teeth, serrations or ridged surfaces 106 (collectively, teeth) along its length. The second plurality of teeth 106 provide for connection to a second portion of the bony structure of the inferior situated vertebra. The sides of the pocket 100 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony vertebral structure.

The flexible spinal spacer 80 is thus configured to provide for various degrees of angulation, flexion, extension and/or compression. Thus, the present flexible spinal spacer allows for controlled movement of the adjacent vertebrae to which it is attached (the superior and inferior situated vertebra), as well as aid in insertion and/or implantation of the flexible spinal spacer.

Figure 10:
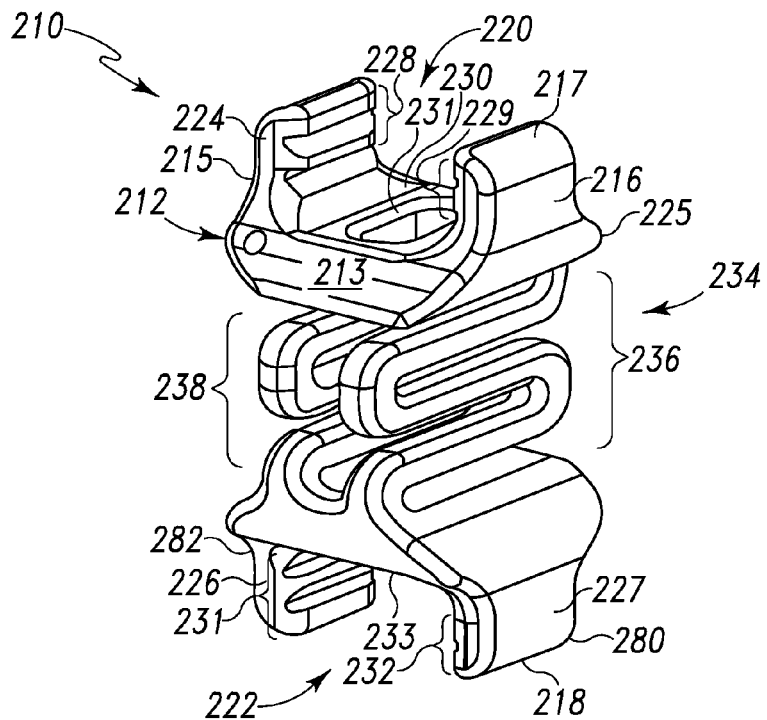
FIG. 10 is an isometric view of another embodiment of a flexible interspinous/inter-laminar spinal spacer (processes, transverse & spinous—i.e. flexible spinal spacer) fashioned in accordance with the principles of the present invention.
Figure 11:
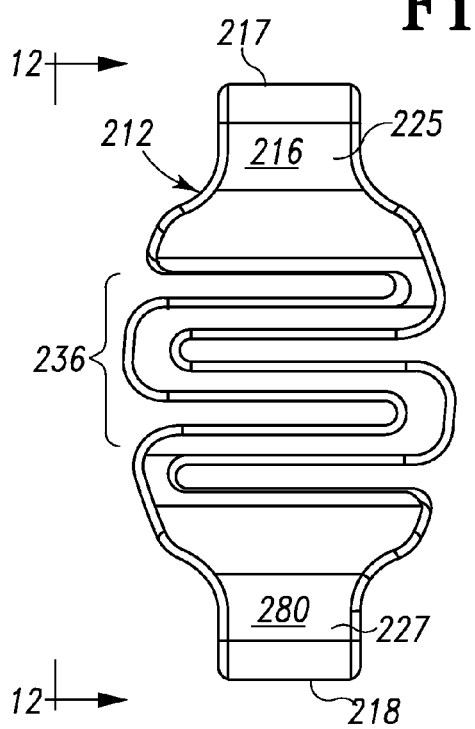
FIG. 11 is a front view of the flexible spinal spacer of FIG. 10.
Figure 12:
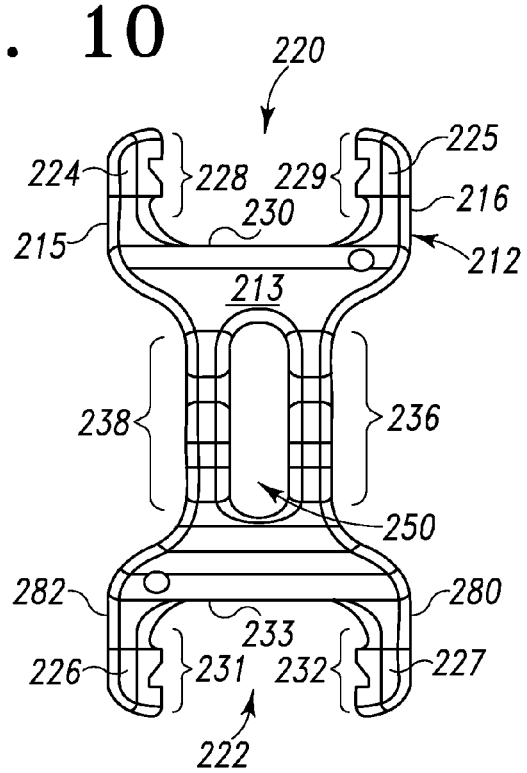
FIG. 12 is a side view of the flexible spinal spacer of FIG. 10 taken along line 12-12 of FIG. 11.

Referring to FIGS. 10-12, there is shown another embodiment of a flexible interspinous or inter-laminar spinal spacer (processes, transverse and spinous—i.e. flexible spinal spacer) generally designated 210 fashioned in accordance with the principles of the present invention. The flexible spinal spacer 210 is used as an interspinous, inter-laminar, interbody, or interbony spinal spacer and thus is configured to be placed between bony structures of adjacent vertebrae of a spine.

The flexible spinal spacer 210 is formed as a unitary or single-piece body 212 of a biocompatible material. The body 212 defines a first superior lateral side 216, a second superior lateral side 215, a first inferior lateral side 280, a second inferior lateral side 282, a posterior side 213, an anterior side opposite the posterior side, a superior side or end 217, and an inferior side or end 218. It should be appreciated that the flexible spinal spacer may take forms other than an "H" while maintaining the features and/or characteristics of the present invention. The body 212 also has a flex portion 234 disposed between the superior side 217 and the inferior side 218. The flex portion 234 has flexure characteristics/properties that provide for relative movement or motion of the spinal spacer 210 and thus motion or movement between the adjacent vertebrae to which it is connected. The flex portion 234 is configurable to provide for various degrees of angulation and/or compression of the body 212.

The flex portion 234 comprises a first flexure contour 236 (e.g. a spring or spring-like contours) defined by and in a lateral side of the unitary body 212 and a second flexure contour 238 (e.g. a spring or spring-like contours) defined by and in the other lateral of the unitary body 212. It should be appreciated that the shape and/or configuration of the flexure contours 236, 238 may be fashioned differently if desired to achieve angulation, flexion, extension and/or compression of the body 212. A cavity 250 is defined between the flexure contours 236, 238. The number of contours and their configuration may vary depending on the desired amount and/or type of flexure and/or flexure properties.

The superior end 217 is formed as a saddle-shape defining first and second legs 224, 225 separated by a pocket 220 that is configured to receive a bony structure of a superior situated vertebra. The first and second legs 224 and 226 define first and second lateral sides of the pocket 220 with a curved bottom 230 having an opening 231 therein. The first lateral side of the pocket 220 has a first plurality of teeth, serrations or ridged surfaces 228 (collectively, teeth) along its length. The first plurality of teeth 228 provide for connection to a first portion of a bony vertebral structure. The second lateral side of the pocket 220 has a second plurality of teeth, serrations or ridged surfaces 229 (collectively, teeth) along its length. The second plurality of teeth 229 provide for connection to a second portion of the bony structure of the superior situated vertebra. The sides of the pocket 220 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony structure of the superior situated vertebra.

The inferior end 218 is formed as a saddle-shape defining third and fourth legs 226, 227 separated by a pocket 222 that is configured to receive a bony structure of an inferior situated vertebra (adjacent to the superior situated vertebra). The third and fourth legs 226 and 227 define first and second lateral sides of the pocket 222 with a curved bottom 223 having an opening therein (not seen). The first lateral side of the pocket 222 has a first plurality of teeth, serrations or ridged surfaces 231 (collectively, teeth) along its length. The first plurality of teeth 231 provide for connection to a first portion of a bony structure of the inferior vertebra. The second lateral side of the pocket 222 has a second plurality of teeth, serrations or ridged surfaces 232 (collectively, teeth) along its length. The second plurality of teeth 232 provide for connection to a second portion of the bony structure of the inferior situated vertebra. The sides of the pocket 222 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony vertebral structure.

The flexible spinal spacer 210 is thus configured to provide for various degrees of angulation, flexion, extension and/or compression. Thus, the present flexible spinal spacer allows for controlled movement of the adjacent vertebrae to which it is attached (the superior and inferior situated vertebra), as well as aid in insertion and/or implantation of the flexible spinal spacer.

Figure 13:
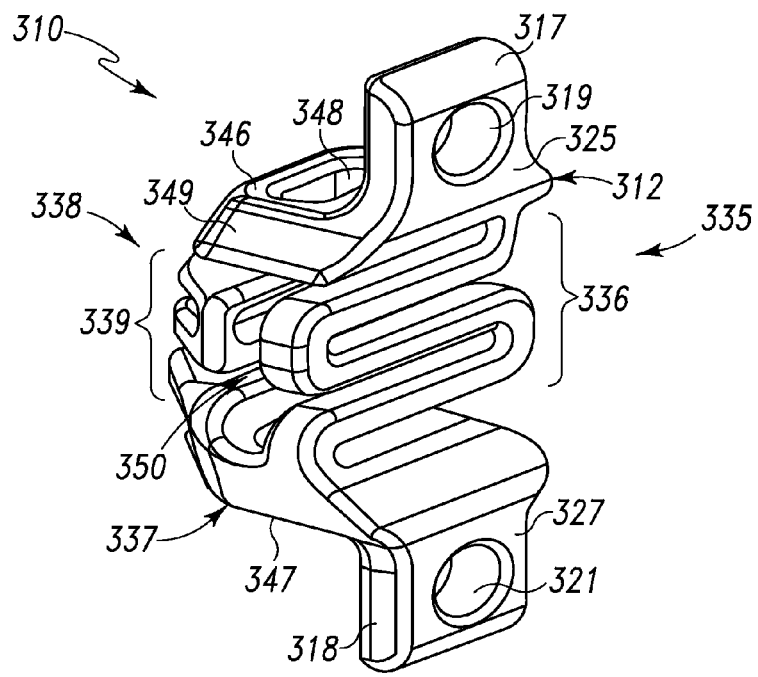
FIG. 13 is an isometric view of another embodiment of a flexible interspinous/inter-laminar spinal spacer (processes, transverse & spinous—i.e. flexible spinal spacer) fashioned in accordance with the principles of the present invention.
Figures 14, 15:
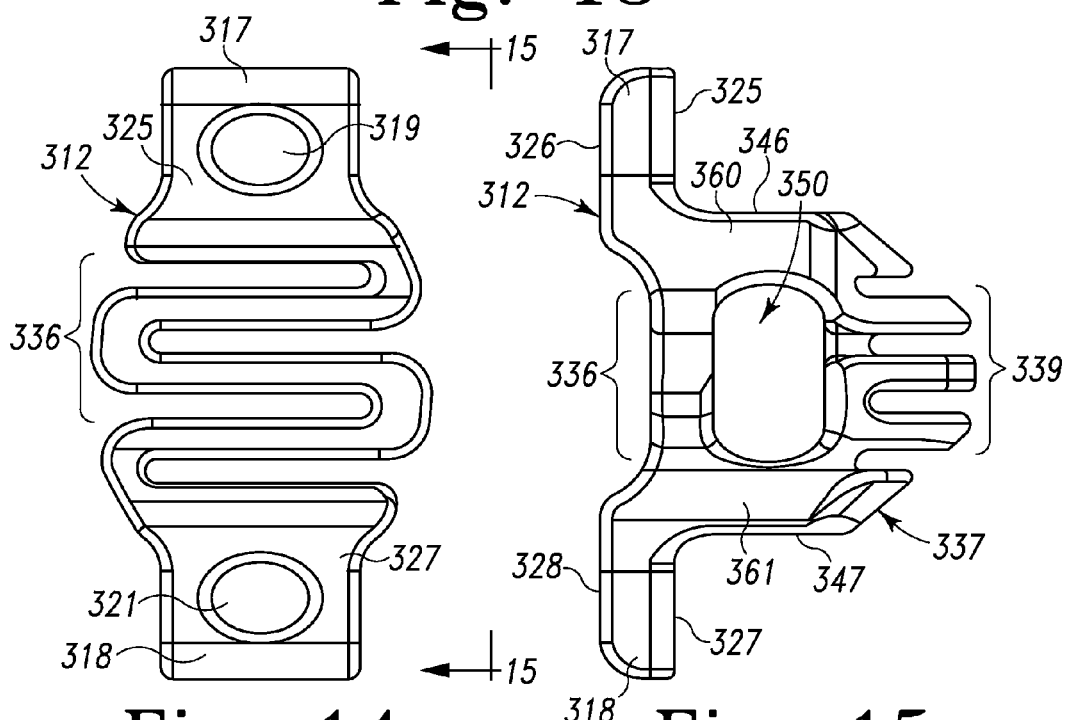
FIG. 14 is a front view of the flexible spinal spacer of FIG. 13.
FIG. 15 is a side view of the flexible spinal spacer of FIG. 13 taken along line 15-15 of FIG. 13.

Referring to FIGS. 13-15, there is shown another embodiment of a flexible interspinous or inter-laminar spinal spacer (processes, transverse and spinous—i.e. flexible spinal spacer) generally designated 310 fashioned in accordance with the principles of the present invention. The flexible spinal spacer 310 is used as an interspinous, inter-laminar, interbody, or interbony spinal spacer and thus is configured to be placed between bony structures of adjacent vertebrae of a spine.

The flexible spinal spacer 310 is formed as a unitary or single-piece body 312 of a biocompatible material. The body 312 has a first flange 317 defining a lateral wall 325 and a second flange 318 defining a lateral wall 327. The first flange 317 has a bore 319 while the second flange 318 has a bore 321. Each bore 319 and 321 allows the reception of bone screw, staple, sutures or other fastening or holding device for securement to the spinous processes. The body 312 also has a flex portion 335 disposed between the first and second flanges 317, 318. The flex portion 335 has flexure characteristics/properties that provide for relative movement or motion of the spinal spacer 310 and thus motion or movement between the adjacent vertebrae to which it is connected. The flex portion 335 is configurable to provide for various degrees of angulation and/or compression of the body 312.

The flex portion 335 comprises a flexure contour 339 (e.g. a spring or spring-like contours) defined by and in a lateral side of the unitary body 312. It should be appreciated that the shape and/or configuration of the flexure contour 339 may be fashioned differently if desired to achieve angulation, flexion, extension and/or compression of the body 312. The number of contours and their configuration may vary depending on the desired amount and/or type of flexure and/or flexure properties.

The body 312 also defines a bullet nose or projection 337 that extends from a first arm 360 and a second arm 361, with the first and second arms 360, the bullet nose 337 and the flex portion 335 defining a cavity 350. The bullet nose 337 includes a plurality of protrusions 339 that are designed to pierce through the interspinous ligament so that the ligament can remain intact for holding the implant in place. The number of protrusions and their configuration may vary as desired.

The flexible spinal spacer 310 is thus configured to provide for various degrees of angulation, flexion, extension and/or compression. Thus, the present flexible spinal spacer allows for controlled movement of the adjacent vertebrae to which it is attached (the superior and inferior situated vertebra), as well as aid in insertion and/or implantation of the flexible spinal spacer.

Figure 16:
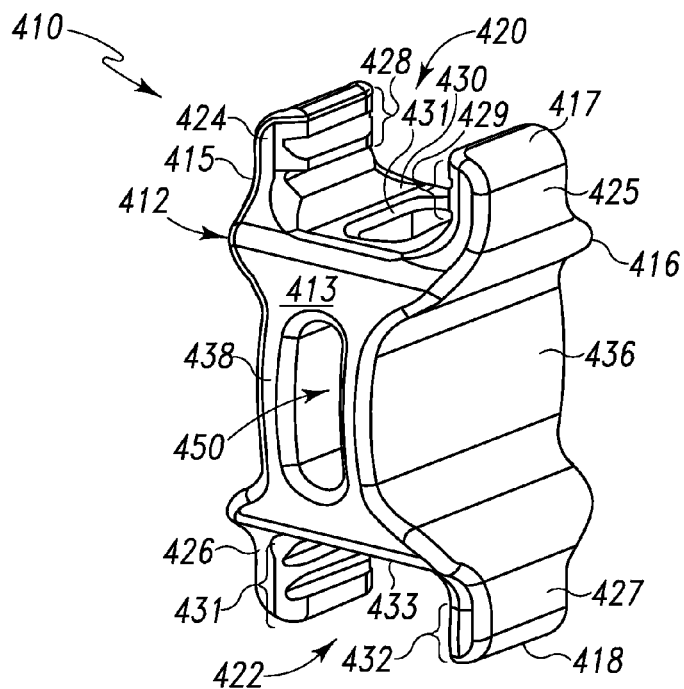
FIG. 16 is an isometric view of a static interspinous/inter-laminar spinal spacer (processes, transverse & spinous—i.e. static spinal spacer) fashioned in accordance with the principles of the present invention.
Figure 17:
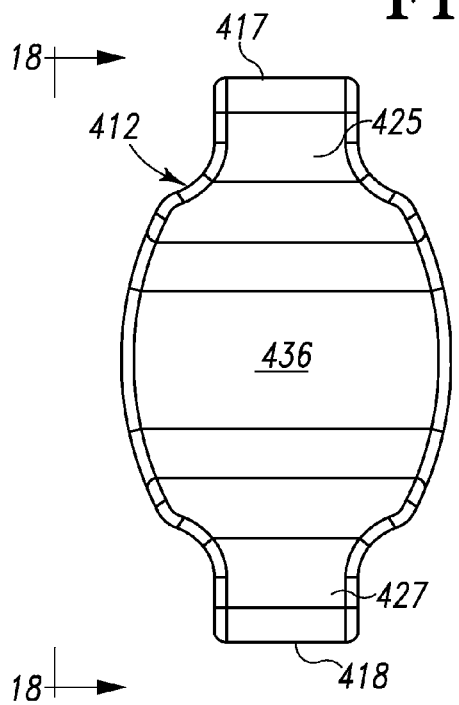
FIG. 17 is a front view of the static spinal spacer of FIG. 16.
Figure 18:
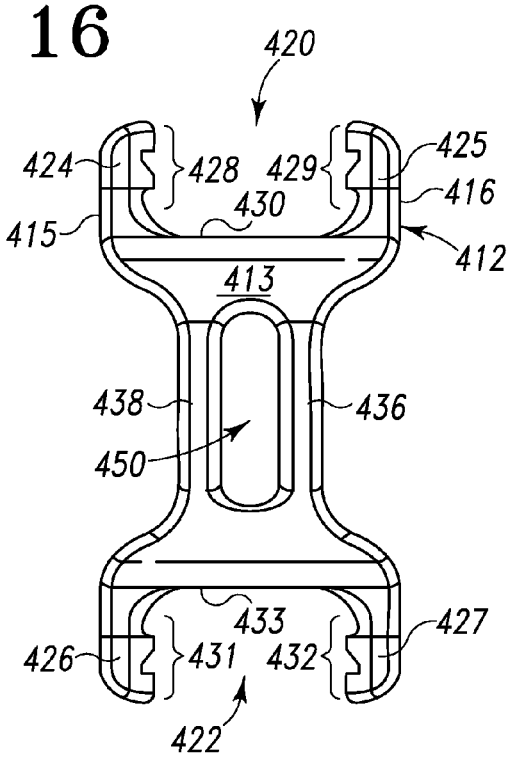
FIG. 18 is a side view of the static spinal spacer of FIG. 16 taken along line 18-18 of FIG. 17.

Referring to FIGS. 16-18, there is shown an embodiment of a static interspinous or inter-laminar spinal spacer (processes, transverse and spinous—i.e. static spinal spacer) generally designated 410 fashioned in accordance with the principles of the present invention. The static spinal spacer 410 is used as an interspinous, inter-laminar, interbody, or interbony spinal spacer and thus is configured to be placed between bony structures of adjacent vertebrae of a spine.

The static spinal spacer 410 is formed as a unitary or single-piece body 412 of a biocompatible material. The body 412 defines a first superior lateral side 416, a second superior lateral side 415, a first inferior lateral side 427, a second inferior lateral side 426, a posterior side 413, an anterior side opposite the posterior side, a superior side or end 417, and an inferior side or end 418. It should be appreciated that the flexible spinal spacer may take forms other than an "H" while maintaining the features and/or characteristics of the present invention.

The superior end 417 is formed as a saddle-shape defining first and second legs 424, 425 separated by a pocket 420 that is configured to receive a bony structure of a superior situated vertebra. The first and second legs 424 and 425 define first and second lateral sides of the pocket 420 with a curved bottom 430 having an opening 431 therein. The first lateral side of the pocket 420 has a first plurality of teeth, serrations or ridged surfaces 428 (collectively, teeth) along its length. The first plurality of teeth 428 provide for connection to a first portion of a bony vertebral structure. The second lateral side of the pocket 420 has a second plurality of teeth, serrations or ridged surfaces 429 (collectively, teeth) along its length. The second plurality of teeth 429 provide for connection to a second portion of the bony structure of the superior situated vertebra. The sides of the pocket 420 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony structure of the superior situated vertebra.

The inferior end 418 is formed as a saddle-shape defining third and fourth legs 426, 427 separated by a pocket 422 that is configured to receive a bony structure of an inferior situated vertebra (adjacent to the superior situated vertebra). The third and fourth legs 426 and 427 define first and second lateral sides of the pocket 422 with a curved bottom 433 having an opening therein (not seen). The first lateral side of the pocket 422 has a first plurality of teeth, serrations or ridged surfaces 431 (collectively, teeth) along its length. The first plurality of teeth 431 provide for connection to a first portion of a bony structure of the inferior vertebra. The second lateral side of the pocket 422 has a second plurality of teeth, serrations or ridged surfaces 432 (collectively, teeth) along its length. The second plurality of teeth 432 provide for connection to a second portion of the bony structure of the inferior situated vertebra. The sides of the pocket 422 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony vertebral structure.

The body 412 has a first sidewall 436 disposed between the first and second legs 424, 425 and the third and fourth legs 426, 427, and a second sidewall 438 disposed between the first and second legs 424, 425 and the third and fourth legs 426, 427. The first and second sidewalls 436, 438 are rigid thus defining a static spinal spacer. A cavity 450 is disposed between the first and second sidewalls 436, 438.

Figure 19:
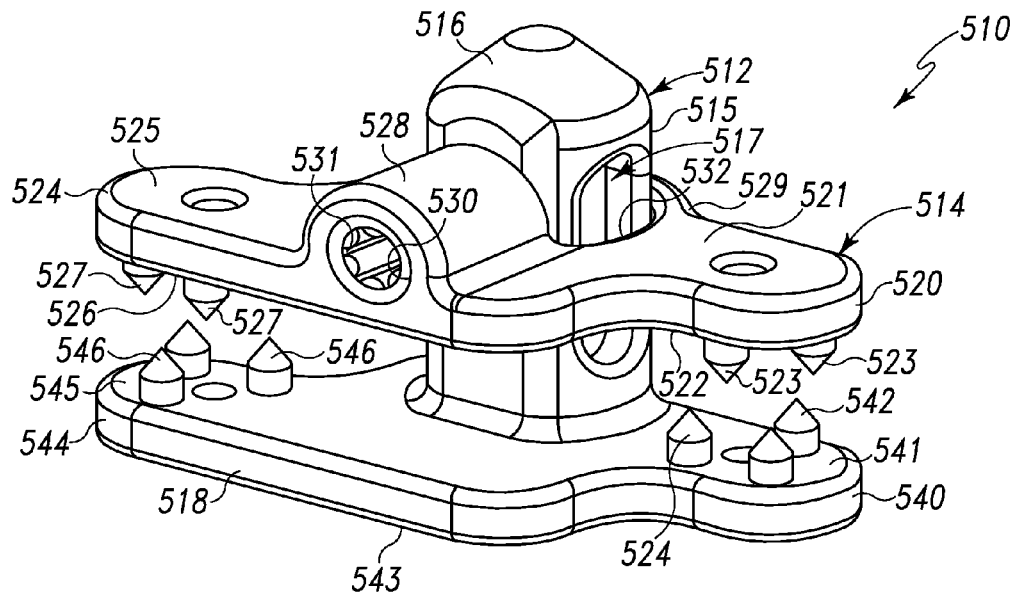
FIG. 19 is an isometric view of another embodiment of a static interspinous/inter-laminar spinal spacer (processes, transverse & spinous—i.e. static spinal spacer) fashioned in accordance with the principles of the present invention.
Figures 20, 21:
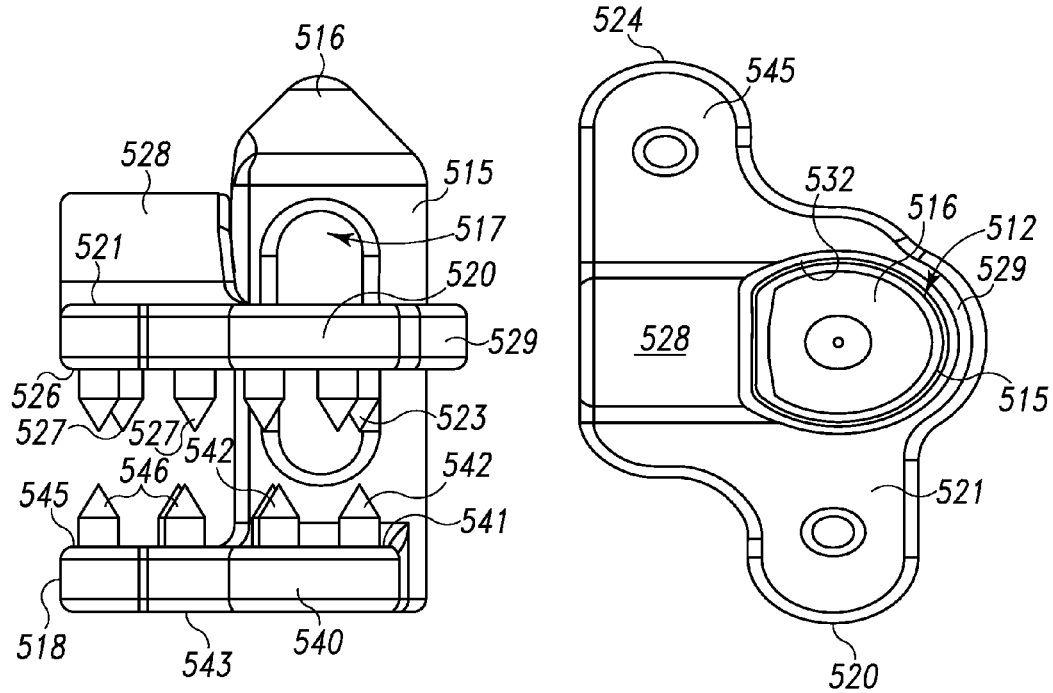
FIG. 20 is a front view of the static spinal spacer of FIG. 19.
FIG. 21 is a side view of the flexible spinal spacer of FIG. 19 taken along line 21-21 of FIG. 20.

Referring now to FIGS. 19-21, there is shown another embodiment of a static interspinous or inter-laminar spinal spacer (processes, transverse and spinous—i.e. static spinal spacer) generally designated 510 fashioned in accordance with the principles of the present invention. The static spinal spacer 510 is used as an interspinous, inter-laminar, inter-body, or interbony spinal spacer and thus is configured to be placed between bony structures of adjacent vertebrae of a spine.

The static spinal spacer 510 is formed by a body 512 having a contoured plate 518 defining a lower surface 543 and having a post 515 extending transverse to the contoured plate 518 from an upper surface thereof. The post 515 has a bullet nose or projection 516 that is designed to pierce through the interspinous ligament so that the ligament can remain intact for holding the implant in place, and an interior cavity 517. The contoured plate 518 has a first wing 540 defining an upper surface 541 having a plurality of spikes 542 or other similar features for engaging the spinous process for securement thereof. The contoured plate 518 also has a second wing 544 defining an upper surface 545 having a plurality of spikes 546 or other similar features for engaging the spinous process for securement thereof.

A second contoured plate 514 having a lateral wall is provided for attachment to the post 515. The second contoured plate 514 has a first wing 520 defining a lower surface 522 having a plurality of spikes 523 or other similar features for engaging the spinous process for securement thereof. The second contoured plate 514 has a second wing 524 defining a lower surface 526 having a plurality of spikes 527 or other similar features for engaging the spinous process for securement thereof. The second contoured plate 514 further has a bore 532 that is sized for reception onto the post 515. The bore 532 defines a rounded rear portion 529 that extends about the post 515. The second contoured plate 514 also has an elongated boss 528 having a bore 530 for securement of the second contoured plate 514 onto the post 515. The second contoured plate 514 is movable up and down the post 515 for proper positioning and securement of the second contoured plate 514. The second contoured plate 514 aids in preventing rotation between the components. A set screw 531 is received in the boss bore 530 that engages the post 515 for fixing the second contoured plate 514 relative to the post 515.

The various spinal spacers are made from a biocompatible material such as PEEK, titanium or stainless steel. Other biocompatible materials or compounds may be used such as bone or an elastomeric or plastic other than PEEK. It should be appreciated that the present flexible spinal spacer may come in various sizes/dimensions to accommodate various spinal anatomies. Also, the body of the present spinal spacers may be other than H-shaped such as triangular or otherwise.

The spinal spacers of the figures are implanted between adjacent bony structures or protrusions (e.g. spinous process/transverse process) through an incision made in the patient proximate the area of implantation. Adjacent vertebrae are distracted and an appropriate spinal spacer is situated between the adjacent structures.

While the invention has been illustrated and described in detail in the drawings and foregoing description, the same is to be considered as illustrative and not restrictive in character, it being understood that only preferred embodiments have been shown and described and that all changes and/or modifications that come within the spirit of the invention are desired to be protected.

What is claimed is:

1. A spinal spacer for insertion into a spinal space between a first vertebra and a second vertebra, the spinal spacer comprising:
 a unitary body comprising:
  a first contoured plate having a first wing configured to engage the first vertebra and a second wing configured to engage the second vertebra;
  a post integral with and extending from the first contoured plate to define a longitudinal axis, the post having an outer surface and a solid bullet nose, wherein the outer surface includes a curved portion and a planar portion;
a second contoured plate slidably coupled to the post of the unitary body, the second contoured plate comprising:
a first wing configured to engage the first vertebra;
a second wing configured to engage the second vertebra;
a rear portion extending between the first wing and the second wing;
a front portion extending between the first wing and the second wing;
wherein the first wing, second wing, rear portion, and front portion define a first bore configured to receive the post; and
wherein the solid bullet nose is designed to pierce through an interspinous ligament between the first vertebra and the second the vertebra so that the interspinous ligament can remain intact for holding the implant in place.

2. The spinal spacer of claim 1, wherein the post further comprises an interior cavity and a second bore through the curved portion of the post to provide access to the interior cavity.

3. The spinal spacer of claim 1, wherein the first bore in the second contoured plate includes a planar portion and a curved portion to correspond with the planar portion and the curved portion on the post.

4. The spinal spacer of claim 3, wherein engagement of the planar and curved portions of the first bore on the second contoured plate with the planar and curved portions on the post inhibit rotation of the second contoured plate relative to the first contoured plate.

5. The spinal spacer of claim 1, wherein the first wing and the second wing of the first contoured plate each comprise a plurality of spikes extending toward the second contoured plate.

6. The spinal spacer of claim 5, wherein the first wing and the second wing of the second contoured plate each comprise a plurality of spikes extending toward the first contoured plate.

7. The spinal spacer of claim 1, wherein the front portion of the second contoured plate comprises a boss having a threaded third bore with an axis perpendicular to the longitudinal axis of the post.

8. The spinal spacer of claim 7, further comprising a screw received in the threaded third bore and configured to engage the planar portion of the post to secure the second contoured plate relative to the unitary body.

9. The spinal spacer of claim 1, wherein the first bore provides a continuous surface that surrounds at least a portion of the outer surface of the post.

10. A method of implanting a spinal spacer through an interspinous ligament and into a spinal space between a first vertebra and a second vertebra, the method comprising:
providing a first contoured plate, a post, a second contoured plate, and a screw, the first contoured plate having a first wing and a second wing, the post integral with and extending from the first contoured plate to define a longitudinal axis, the post having a solid bullet nose and an outer surface with a curved portion and a planar portion, the second contoured plate slidably coupled to the post and having a first wing, a second wing, a rear portion between the first wing and the second wing, and a bore to receive the post;
pushing the bullet nose through the interspinous ligament;
inserting the post in the spinal space between the first vertebra and the second vertebra;
inserting the second contoured plate onto the post.

11. The method of claim 10, wherein the step of inserting the second contoured plate onto the post comprises aligning a planar portion and a curved portion of the bore on the second contoured plate with the planar portion and the curved portion on the post.

12. The method of claim 10, further comprising sliding the second contoured plate along post so that the first wing and the second wing engage the first and second vertebra.

13. A spinal spacer for insertion into a spinal space between a first vertebra and a second vertebra, the spinal spacer comprising:
a body comprising:
a first contoured plate having a first wing configured to engage the first vertebra and a second wing configured to engage the second vertebra;
a post extending from the contoured plate along a longitudinal axis, the post having a curved portion, a planar portion, and a bullet nose configured to pierce through an interspinous ligament between the first vertebra and the second the vertebra so that the interspinous ligament can remain intact for holding the implant in place;
a second contoured plate slidably received on the post, the second contoured plate comprising:
a first wing configured to engage the first vertebra;
a second wing configured to engage the second vertebra;
a rear portion extending between the first wing and the second wing;
a boss having a threaded first bore with an axis perpendicular to the longitudinal axis of the post;
wherein the first wing, second wing, rounded rear portion, and boss define a second bore configured to receive the post,
wherein the second bore includes a planar portion and a curved portion such that engagement of the planar and curved portions of the second bore on the second contoured plate with the planar and curved portions on the post inhibit rotation of the second contoured plate relative to the first contoured plate;
a screw received in the threaded first bore in the boss and engaged with the planar portion of the post to secure the second contoured plate relative to the first contoured plate.

14. The spinal spacer of claim 13, wherein the post further comprises an interior cavity and a third bore through the curved portion of the post to provide access to the interior cavity.

15. The spinal spacer of claim 13, wherein the first wing and the second wing of the first contoured plate each comprise a plurality of spikes extending toward the second contoured plate.

16. The spinal spacer of claim 13, wherein the first wing and the second wing of the second contoured plate each comprise a plurality of spikes extending toward the first contoured plate.

17. The spinal spacer of claim 13, wherein the first bore provides a continuous surface that surrounds at least a portion of the outer surface of the post.

* * * * *